(12) United States Patent
Solar et al.

(10) Patent No.: US 6,740,104 B1
(45) Date of Patent: May 25, 2004

(54) ENHANCED CATHETER WITH ALIGNMENT MEANS

(75) Inventors: Ronald J. Solar, San Diego, CA (US); Glen L. Lieber, Poway, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 52 days.

(21) Appl. No.: 09/629,768

(22) Filed: Jul. 31, 2000

Related U.S. Application Data

(63) Continuation-in-part of application No. 09/454,255, filed on Dec. 2, 1999, now Pat. No. 6,447,501, which is a continuation-in-part of application No. 09/312,529, filed on May 14, 1999, now Pat. No. 6,394,995.
(60) Provisional application No. 60/085,636, filed on May 15, 1998.

(51) Int. Cl.[7] .................. A61M 31/00; A61M 25/01; A61M 25/02; A61M 25/04; A61M 25/06; A61M 25/08; A61M 25/082; A61M 25/085; A61M 25/088; A61M 25/09; A61M 25/095; A61M 25/098; A61M 29/00
(52) U.S. Cl. .................... 606/194; 604/510; 604/95.04; 604/528; 604/509
(58) Field of Search .................. 604/500, 509, 604/510, 95.04, 96.01, 103.04, 103.05, 103.09, 264, 265–266, 523, 524, 525, 526–527, 528, 921; 606/191–194

(56) References Cited

U.S. PATENT DOCUMENTS

| 3,811,448 A | 5/1974 | Morton |
| 4,195,637 A | 4/1980 | Gruntzig et al. |
| 4,323,071 A | 4/1982 | Simpson et al. |
| RE31,800 E | 1/1985 | Lauterjung |
| 4,493,711 A | 1/1985 | Chin et al. |

(List continued on next page.)

Primary Examiner—Brian L. Casler
Assistant Examiner—Catherine S. Williams
(74) Attorney, Agent, or Firm—Reed Smith LLP; William H. Dippert

(57) ABSTRACT

A balloon dilatation system is comprised of an elongated flexible advancement member which terminates in a tubular tracking member slidable over a guidewire. An inflatable balloon has proximal and distal ends, the proximal end communicating with an inflation channel, and the distal end attaching to the tracking member. The balloon portion is coextensive with but not attached to the advancement member. An alignment member aligns the advancement member and the inflation channel. Other embodiments relate to delivery of stents or other medical instrumentalities.

43 Claims, 8 Drawing Sheets

U.S. PATENT DOCUMENTS

| | | | |
|---|---|---|---|
| 4,573,470 A | | 3/1986 | Samson et al. |
| 4,619,263 A | | 10/1986 | Frisbie et al. |
| 4,641,649 A | | 2/1987 | Walinsky et al. |
| 4,643,186 A | | 2/1987 | Rosen et al. |
| 4,748,982 A | | 6/1988 | Horzewski et al. |
| 4,762,129 A | | 8/1988 | Bonzel |
| 4,790,315 A | | 12/1988 | Mueller et al. |
| 4,798,193 A | | 1/1989 | Giesy et al. |
| 4,824,435 A | | 4/1989 | Giesy et al. |
| 5,003,990 A | | 4/1991 | Osypka |
| 5,040,548 A | | 8/1991 | Yock |
| 5,045,061 A | | 9/1991 | Seifert et al. |
| 5,061,273 A | | 10/1991 | Yock |
| 5,090,957 A | * | 2/1992 | Moutafis et al. ............... 600/18 |
| 5,090,958 A | | 2/1992 | Sahota |
| 5,324,257 A | | 6/1994 | Osborne et al. |
| 5,324,259 A | * | 6/1994 | Taylor et al. ............ 604/99.04 |
| 5,395,332 A | | 3/1995 | Ressemann et al. |
| 5,413,557 A | | 5/1995 | Solar |
| 5,415,634 A | | 5/1995 | Glynn et al. |
| 5,505,702 A | * | 4/1996 | Arney ................... 604/101.01 |
| 5,540,659 A | | 7/1996 | Teirstein |
| 5,569,199 A | | 10/1996 | Solar |
| 5,571,087 A | * | 11/1996 | Ressemann et al. ..... 604/96.01 |
| 5,575,771 A | * | 11/1996 | Walinsky ................. 604/96.01 |
| 5,578,009 A | | 11/1996 | Kraus et al. |
| 5,605,543 A | * | 2/1997 | Swanson ............... 604/102.02 |
| 5,667,493 A | | 9/1997 | Janacek |
| 5,667,521 A | | 9/1997 | Keown |
| 5,690,642 A | | 11/1997 | Osborne et al. |
| 5,706,827 A | * | 1/1998 | Ehr et al. ................... 600/585 |
| 5,718,680 A | | 2/1998 | Kraus et al. |
| 5,728,067 A | | 3/1998 | Enger |
| 5,730,698 A | | 3/1998 | Fischell et al. |
| 5,752,932 A | * | 5/1998 | Ellis et al. ............... 604/96.01 |
| 5,863,285 A | | 1/1999 | Coletti |
| 5,879,305 A | | 3/1999 | Yock et al. |
| 5,882,334 A | | 3/1999 | Sepetka et al. |
| 6,071,285 A | | 6/2000 | Lashinski et al. |
| 6,394,995 B1 | * | 5/2002 | Solar et al. ................. 604/528 |
| 6,447,501 B1 | * | 9/2002 | Solar et al. ................. 604/528 |
| 6,500,147 B2 | * | 12/2002 | Omaleki et al. ....... 604/103.09 |

* cited by examiner

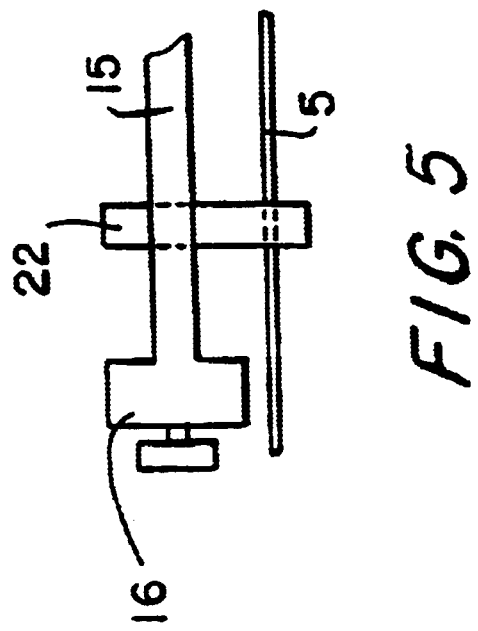
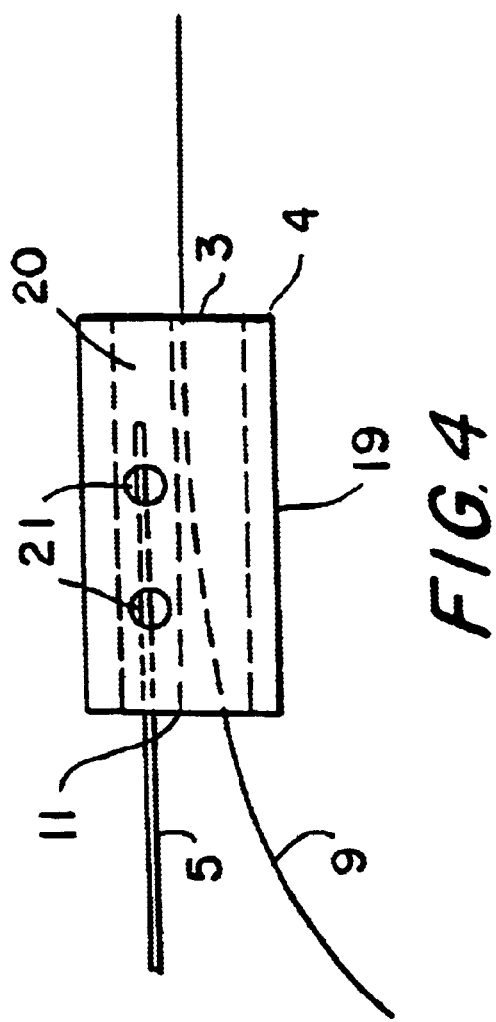

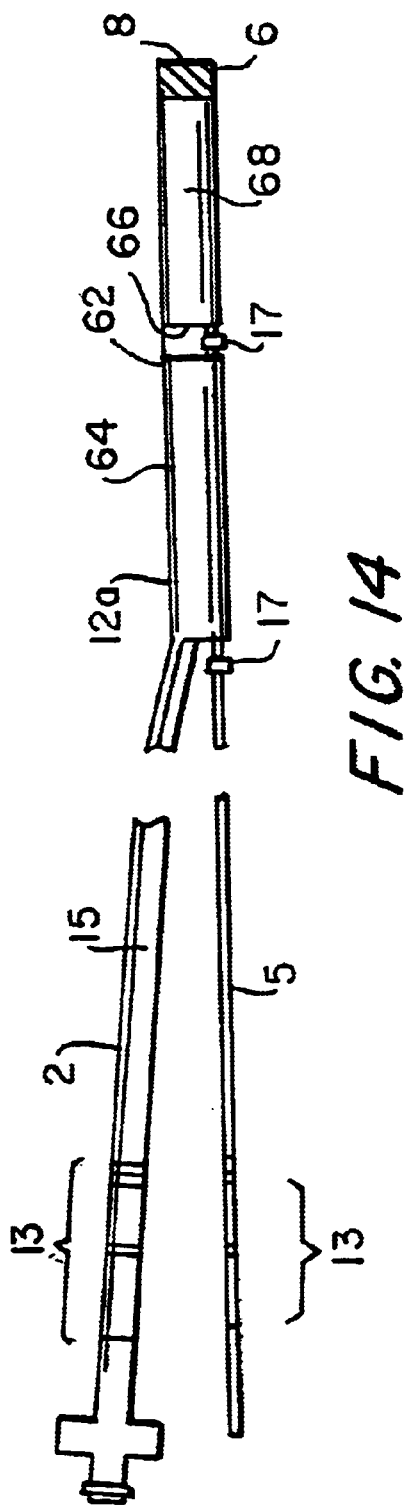
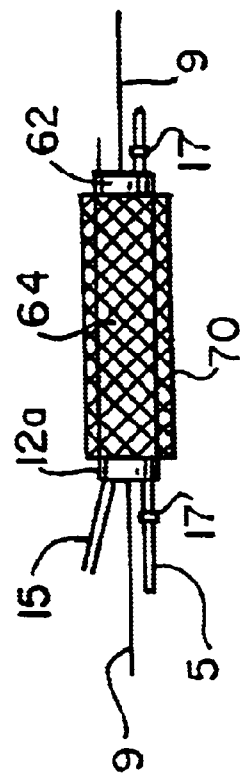
FIG. 14
FIG. 15

ENHANCED CATHETER WITH ALIGNMENT MEANS

CROSS-REFERENCE TO RELATED APPLICATIONS

This application is a continuation-in-part of U.S. patent application Ser. No. 09/454,255, filed, Dec. 2, 1999, now U.S. Pat. No. 6,447,501 B1, which is a continuation-in-part of U.S. patent application Ser. No. 09/312,529, filed May 14, 1999, now U.S. Pat. No. 6,394,995 which is based upon U.S. provisional patent application Serial No. 60/085,636, filed May 15, 1998.

SCOPE OF THE INVENTION

This invention relates to the fields of angioplasty and other interventional procedures. More particularly, this invention relates to improved balloon dilatation systems where the distal end of the inflatable dilatation balloon is attached to a tubular tracking member or an advancement member and alignment means align the tracking member and an inflation channel.

BACKGROUND OF THE INVENTION

Balloon dilatation catheters have been used to dilate various types of strictures in blood vessels and other body lumens for over twenty years. Typically, such catheters comprise a balloon mounted on the distal end of an elongated flexible shaft and an inflation tube or lumen extending longitudinally within the shaft from its proximal end to the interior of the balloon. Among the major advancements in balloon dilatation catheters have been the development of smaller catheters that can be used in smaller and/or more distal anatomical locations, and the development of catheters that can be rapidly exchanged. Examples of such catheters are described in U.S. Pat. Nos. 4,748,982 (Horzewski), 4,762,129 (Bonzel), 5,040,548 (Yock), 5,061,273 (Yock), 5,569,199 (Solar) and 5,728,067 (Enger). Because these catheters have become more sophisticated and complex in design, and despite the manufacturers' experience in manufacturing them, these catheters are expensive to make. Furthermore, despite these improvements, difficulties are still encountered in advancing catheters through tortuous anatomy and safely crossing very tight strictures and stenoses in the vascular system and other body lumens or cavities.

Recently vascular stents have been shown to play an important role in reducing the restenosis rates associated with balloon angioplasty. However, stents are sometimes lost from the delivery systems and are difficult to retrieve safely. In addition, stents cannot completely overcome the trauma and injury that result from balloon dilatation. Thus, there is a need for enhanced balloon dilatation catheters.

OBJECTS OF THE INVENTION

It is an object of the invention to provide an enhanced dilatation system that is extremely low-profile to more easily and safely cross very tight strictures and stenoses in the vascular system and other body lumens or cavities.

It is also an object of the invention to provide an enhanced dilatation system that provides for an improved means for crossing tight stenoses, as well as to navigate tortuous anatomy.

It is another object of the invention to provide an enhanced dilatation system that has the ability to be exchanged rapidly.

It is yet another object of the invention to provide an enhanced dilatation system that can be used to retrieve dislodged stents.

It is a further object of the invention to provide an enhanced dilatation system that can be manufactured inexpensively and more reliably then currently available balloon dilatation systems.

It is also an object of the invention to provide an enhanced dilatation system that allows placement of an additional catheter or instrumentality adjacent to a catheter.

It is likewise an object of the invention to provide an enhanced dilatation system that facilitates placement of stents or stent grafts.

It is a yet further object of the invention to provide a balloon catheter system and a stent delivery system having a smaller profile for crossing tight stenoses.

These and other objects of the invention will become more apparent from the discussion below.

SUMMARY OF THE INVENTION

According to the invention, an enhanced balloon dilatation delivery system comprises an elongated advancement member which optionally terminates in a tubular tracking member, an inflatable dilatation balloon having proximal and distal ends and being in fluid communication with an inflation channel, and means for aligning the advancement member and the inflation channel. The proximal end of the inflatable balloon is in fluid communication with the inflation channel, and the distal end of the inflatable balloon is attached to the tubular tracking member or the advancement member. During advancement of the system, the inflatable dilatation balloon and inflation channel are somewhat coextensive with the advancement member. The system is slidable over a guidewire.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which:

FIG. 4 is an enlarged illustration of the distal portion of an additional embodiment of the invention;

FIG. 5 is an enlarged illustration of the proximal portion of an alternate embodiment of the invention;

FIGS. 12, 13 and 14 are each a schematic representation of another embodiment of the invention; and FIG. 15 is a detail of FIG. 14.

DETAILED DESCRIPTION OF THE INVENTION

Figure 1:
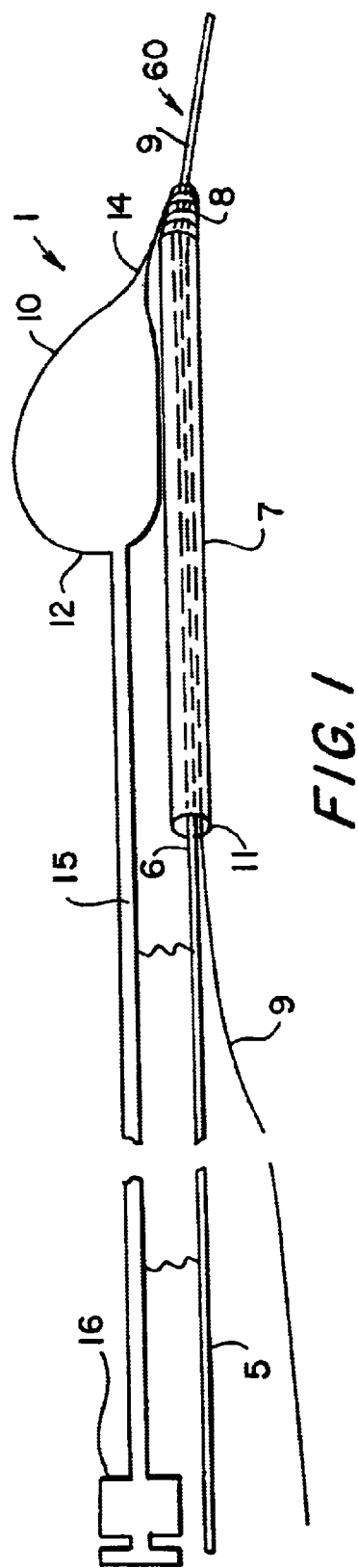
FIGS. 1 to 3 are each a schematic, lateral view of an embodiment of the invention.
Figure 2:
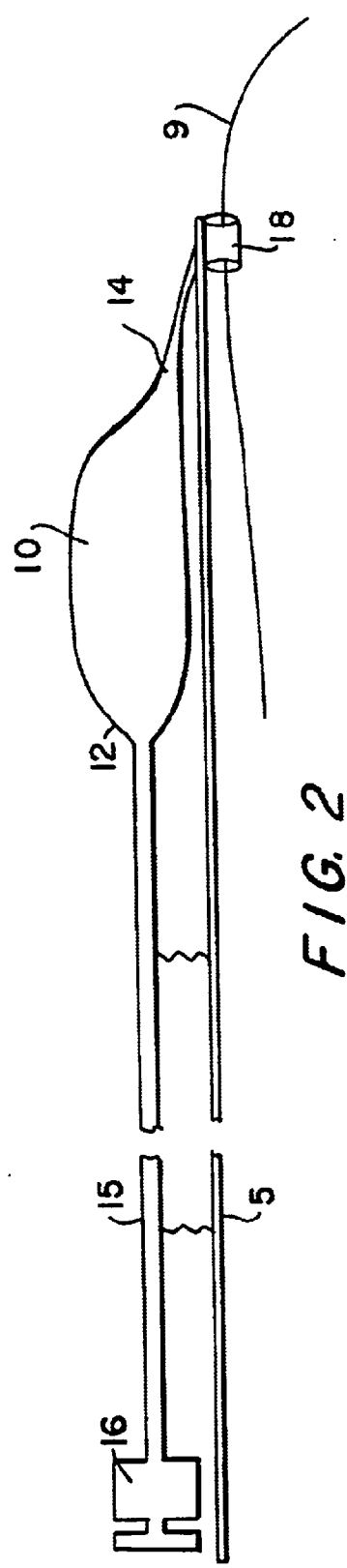
Figure 3:
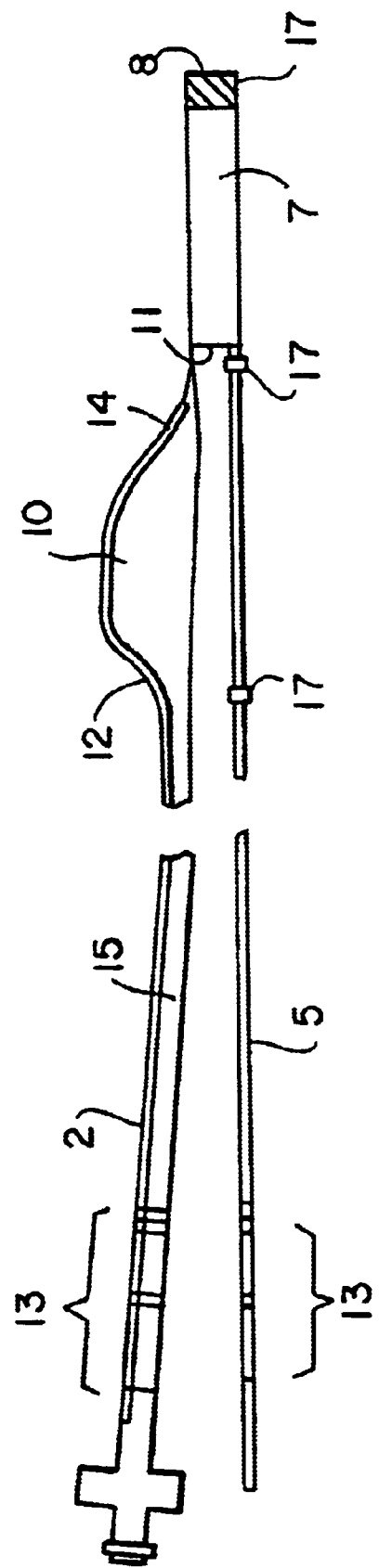

With reference to FIGS. 1 to 3, an enhanced catheter system, designated generally as 1, has an elongated advancement member 5. Preferably advancement member 5 is formed of a flexible wire or, alternately, of spring hollow hypotubing. Advancement member 5 preferably has a diameter of from about 0.008" to 0.035", which diameter could be larger or smaller depending on the application. Advancement member 5 has sufficient column strength and flexibility to provide for advancement of the catheter through tortuous anatomy. Preferably, advancement member 5 is rigid at its proximal end and becomes increasingly more flexible as it extends distally. This may be accomplished by a number of ways known in the art, including, but not limited to, tapering, selective heat treatment and/or forming advancement member 5 from a composite of materials with various properties.

Advancement member 5 terminates at its distal end 6 in an elongated tubular tracking member 7. Tracking member 7 has a tubular configuration and is adapted to slide over a standard guidewire 9 to allow system 1 to advance easily to a desired location within a patient's body. Tracking member 7 has an open proximal end 11 and an open distal end 8, and is preferably formed of a flexible polymeric tube, a spring coil, or a combination thereof. Tracking member 7 is preferably about 10 to 50 cm long and has an inner diameter that is sized to accommodate guidewire 9, most preferably approximately from about 0.012" to 0.040". Optionally tracking member 7 has an inner, outer, or inner and outer coating with a lubricious material to aid in its movement over the guidewire. Lubricious materials for this purpose are well-known in the art.

Advancement member 5 and tracking member 7 are attached by any suitable means known in the art, such as by fusion or a non-toxic adhesive. Alternatively, advancement member 5 and tracking member 7 may be integrally formed during manufacture.

System 1 also has an inflatable balloon 10 having a proximal end 12 and distal end 14. Distal end 14 of balloon 10 is attached to tracking member 7 by any suitable means known in the art, such as by fusion, adhesive bonding or integral formation, and moves therewith. Distal end 14 of balloon 10 may be attached to distal end 8 of tracking member 7, as shown in FIG. 1, or preferably, distal end 14 of balloon 10 is attached to the proximal end 11 of tracking member 7, as shown in FIG. 3. Balloon 10 is formed of a very thin-walled, preferably less than 0.001" thick, polymeric material. Balloon 10 may be formed of any one of a variety of suitable materials known in the art. Optionally balloon 10 may be suitable for dilatation and/or deployment of a stent.

Proximal end 12 of balloon 10 communicates with an elongated inflation channel 15 that extends proximally through a corporeal lumen. Inflation means 15 is formed preferably of a polymeric tubular film that will allow inflation channel 15 to collapse to a smaller profile when not being used for inflation of balloon 10. The wall thickness of inflation channel 15 should preferably be less than 0.001". When inflated, inflation channel 15 will have a diameter of approximately 0.010" or more, depending upon the application. Alternatively, inflation channel 15 may be fabricated out of a non-collapsible tubing material as would be familiar to one skilled in this art. As shown in FIG. 3, inflation channel 15 may have position markers 13 on its proximal portion. Position markers 13, which may be applied by ink or other suitable means known in the art, correspond to similar markers on advancement member 5. Such markers provide visual confirmation of concurrent movement of inflation channel 15 and advancement member 5 during advancement and withdrawal of system 1.

Inflation channel 15 has a hub 16 at its opposite, proximal end. Hub 16 is a standard LUER® lock connector that allows connection of inflation means 15 to standard balloon inflator devices or syringes (not shown). By this means, balloon 10 is in fluid communication with an inflator.

As noted above, distal end 14 of inflatable balloon 10 is attached to tubular tracking member 7. In this way, as tubular tracking member 7 travels through the body along the path of guidewire 9, inflatable balloon 10 is pulled along with tracking member 7 to the desired site. However, although balloon 10 lies coextensively with advancement member 5 (FIGS. 2 and 3) and/or tracking member 7 (FIG. 1), it is unattached to advancement member 5. In this most preferred embodiment of least attachment, pushing on advancement member 5 causes balloon 10 to be easily pulled through the anatomy and tight strictures and stenoses. Since the balloon is not being pushed through a stenosis, there is no tendency for the balloon to compress longitudinally and increase in profile and bulk. Such an occurrence, which may be found in prior art catheters where the balloon is attached proximally and distally to the catheter shaft, can impede advancement and crossing, as well as result in vascular trauma and clinical complications. Since there is no bulky catheter structure within the interior of the balloon (as is found in prior art catheters), the very thin balloon material can easily fold and conform as required to cross a stenosis with minimal friction and trauma as it is pulled across by the tracking member.

As shown in FIG. 3 a wire 2 can optionally extend at least partially within the inflation channel 15 to the distal end 14 of balloon 10. Wire 2 may provide support to the inflation channel 15 and balloon 10 which may be required in some applications. The support wire may be permanently mounted, or alternatively, it may be removable and used as needed. Also, as shown in FIG. 3, the dilatation system may have radiopaque markers 17 to allow the system's position to be monitored, and the proximal ends of the advancement member 5 and/or inflation channel 15 may have one or more visual markers 13 to indicate the lengths inserted. The radiopaque markers may be comprised of conventional radiopaque materials such as gold or platinum, and the visual markers may be comprised of physiological acceptable inks or coatings, preferably in bright or fluorescent colors.

Figure 7:
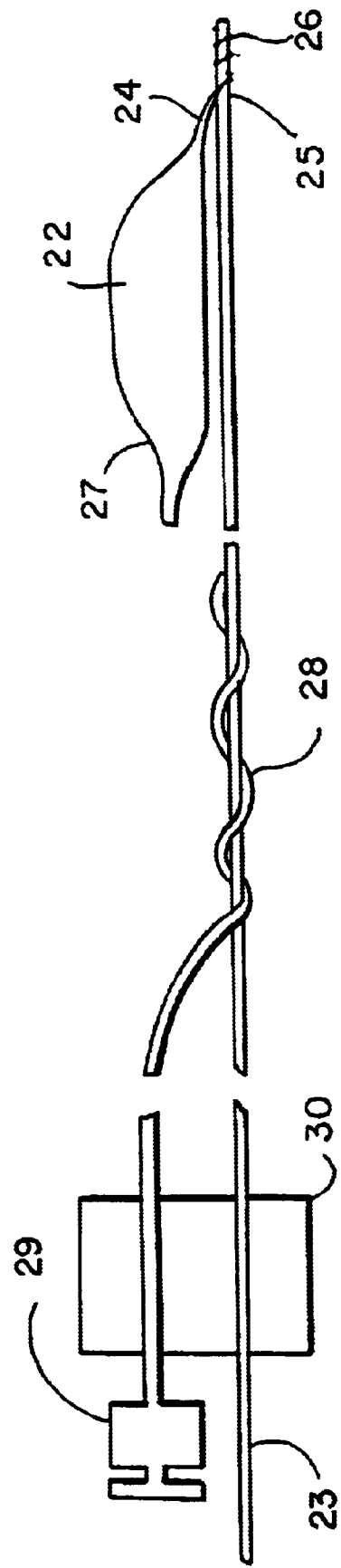

The embodiment of the invention shown in FIG. 7 has an inflatable balloon 22 and a flexible, torqueable, advancement member 23. The distal portion 24 of balloon 22 is fixedly attached to the distal end 25 of advancement member 23. Advancement member distal end 25 may optionally have a flexible spring tip 26.

The proximal portion 27 of balloon 22 is in fluid communication with an inflation channel or means 28 having a hub 29 for connection to an inflation source (not shown). Inflation channel 28 preferably is attached to or wound about advancement member 23 in spiral fashion, in such a way to lower the profile of the system but to not interfere with the fluid communication.

A torquer or rotator member 30 may optionally grip the proximal portion of advancement member 23 and inflation channel 28, to allow radial positioning of advancement member 23. In this embodiment it is preferred that the inflation means spirally wrap around the advancement member. Turning the proximal end of the advancement member with torquer 30 will allow distal end 25 of the advancement member 23 to be positioned at a desired radial location relative to balloon 22 within a corporeal lumen. A torquer 30 could also be used with the embodiments shown in FIGS. 1 and 2, where the tracking means and advancement means would be radially positioned.

Figure 9:
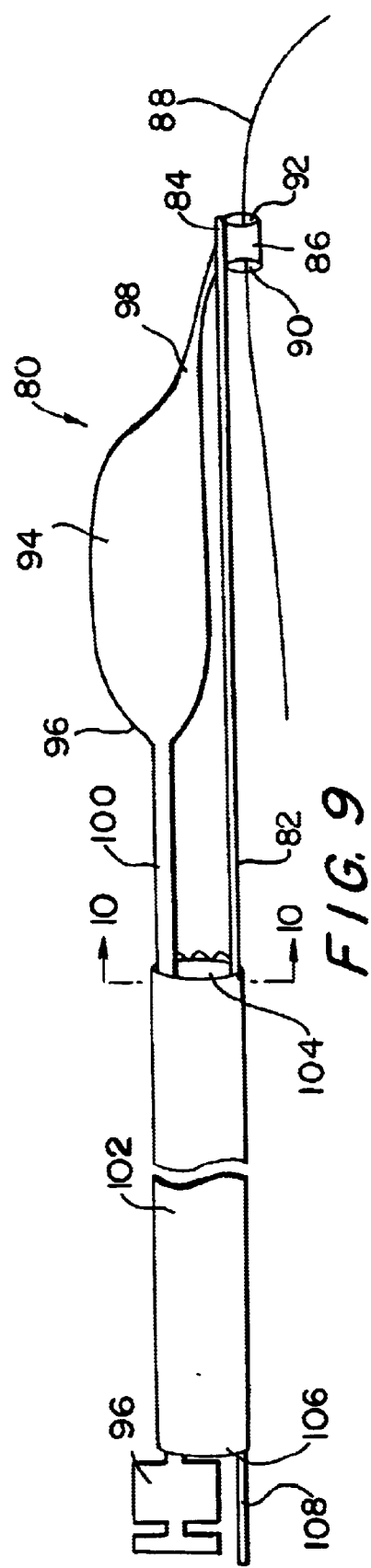
FIG. 9 is a schematic, partly cross-sectional view of another embodiment of the invention

In FIG. 9, an enhanced balloon dilatation system, designated generally as 80, has an elongated advancement member 82. Preferably advancement member 82 is formed of a flexible wire or, alternately, of spring hollow hypotubing, and has the characteristics described above.

Advancement member 82 terminates at its distal end 84 in a tubular tracking member 86. Tracking member 86 has a tubular configuration and is adapted to slide over a standard guidewire 88 to allow system 80 to advance easily to a desired location within a patient's body. Tracking member 86 has an open proximal end 90 and an open distal end 92, and is preferably formed of a flexible polymeric tube, a spring coil, or a combination thereof. Tracking member 86 is preferably about 3 to 30 cm long and has an inner diameter that is sized to accommodate guidewire 88, most preferably approximately from about 0.012" to 0.040". Optionally tracking member 86 has an inner, outer, or inner and outer coating with a lubricious material to aid in its movement over the guidewire.

Advancement member 82 and tracking member 86 are attached by any suitable means known in the art, such as by fusion or a non-toxic adhesive, or, alternatively, have been integrally formed during manufacture.

System 80 also has an inflatable balloon 94 having a proximal end 96 and distal end 98. Distal end 98 of balloon 94 is attached to advancement member 82 or tracking member 86 by any suitable means known in the art, such as by fusion, adhesive bonding or integral formation, and moves therewith. Distal end 98 of balloon 94 may be attached to advancement member 82, as shown in FIG. 9, or optionally distal end 98 of balloon 94 can be attached to the proximal end 90 of tracking member 86, as similar to the arrangement shown in FIG. 3. Balloon 94 is formed of a very thin-walled, preferably less than 0.001" thick, polymeric material, of any one of a variety of suitable materials known in the art.

Proximal end 96 of balloon 94 communicates with an elongated inflation channel 100 that extends proximally through a corporeal lumen. Inflation channel 100 is formed preferably of a polymeric tubular film that will allow inflation channel 100 to collapse to a smaller profile when not being used for inflation of balloon 94. When inflated, inflation channel 100 will have a diameter of approximately 0.010" or more, depending on the application. Alternatively, inflation channel 100 may be fabricated out of a non-collapsible tubing material as would be familiar to one skilled in this art.

Inflation channel 100 has a hub 101 at its opposite, proximal end. Hub 101 is a standard LUER® lock connector that allows connection of inflation channel 100 to standard balloon inflator devices or syringes (not shown). By this means, balloon 94 is in fluid communication with an inflator.

An alignment member or sheath 102 extends longitudinally, whereby it encompasses at least inflation channel 100. Alignment member 102 preferably is attached to or integral with advancement member 82, and preferably advancement member 82 also is encompassed by alignment member 102. Alignment member 102 can be comprised of any suitable flexible or substantially flexible medically acceptable material, such as a polymer or metal. In a preferred embodiment alignment sheath comprises a stainless steel hypotube and advancement member 82 is bonded to its inner or outer surface.

The distal end 104 of alignment member 102 is open, and the proximal end 106 of alignment member 102 is optionally attached to hub 101, optionally with an opening for the proximal portion 108 of advancement member 82.

Figure 11:
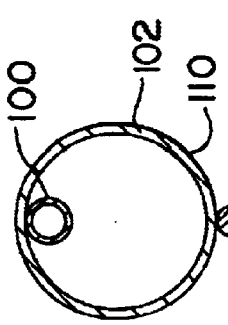
FIG. 11 is an alternate cross-sectional view of FIG. 10.
Figure 10:
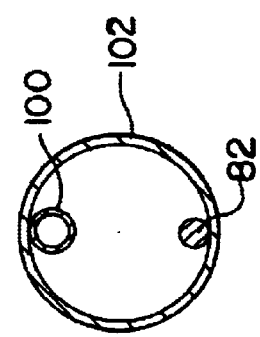
FIG. 10 is a cross-sectional view across line 10—10.

In the cross-sectional view along line 10—10 in FIG. 9 that is represented by FIG. 10, advancement member 82 and inflation channel 100 are positioned within alignment member 102. However, in an alternative embodiment reflected in FIG. 11, advancement member 82 is attached to the outer surface 110 of alignment member 102.

In a preferred embodiment the advancement member has a proximal portion and a distal portion. The proximal portion has at least one lumen having open ends. Inflation channel 100 is positioned within one of said lumens and the proximal portion of the advancement member functions as the alignment member. The distal portion of the advancement member extends distally from the distal end of the proximal portion of the advancement member.

Figure 12:
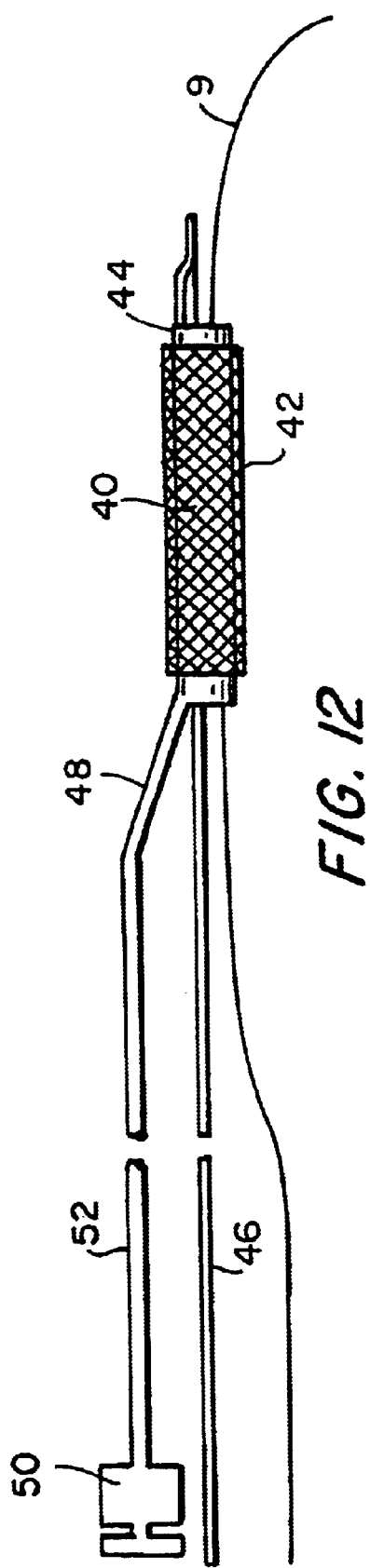

In a preferred embodiment of the invention a stent or stent graft may be delivered. An example of this preferred embodiment is shown in FIG. 12. In this embodiment, an inflatable balloon 40 is folded and formed into a tubular shape, and a stent or stent graft 42 is mounted onto the balloon by various methods known in the art such as, for example, crimping, interference fit, or encapsulation. See, for example, U.S. Pat. Nos. 4,800,882 and 5,836,965. In this embodiment, the distal end 44 of balloon 40 is attached to advancement means 46 adjacent to the distal end of advancement means 46, and the balloon/stent assembly 40/42 acts as a tracking member. The proximal end 48 of balloon 40 is in fluid communication with hub 50 through flexible conduit 52.

Figure 13:
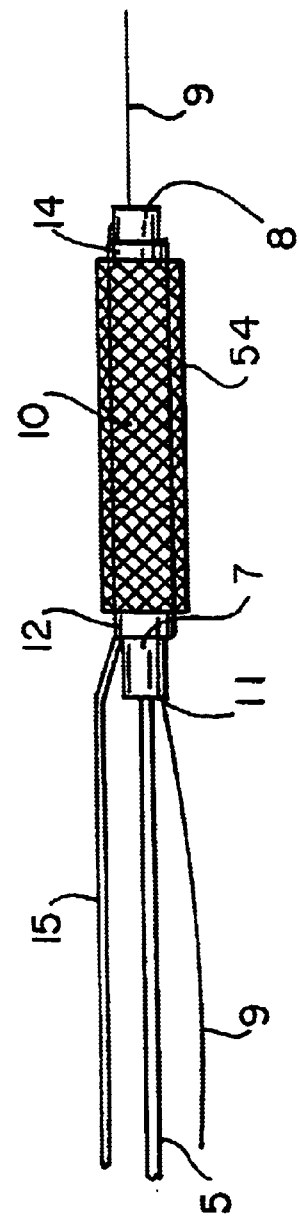

Alternatively, the embodiment illustrated in FIG. 1 may be used to deliver a stent or stent graft. With the distal end 14 of balloon 10 attached to the distal end 8 of the tracking member 7, the balloon is folded around tracking member 7, and the stent/stent graft 54 is mounted onto the folded balloon (FIGS. 1 and 13). Tracking member 7 is advanced over guidewire 9.

In the embodiment shown in FIGS. 14 and 15, the distal end 62 of an inflatable balloon 64 is attached to the proximal end 66 of a tracking member 68. Balloon 64 is folded and formed into a tubular shape, and a stent or stent graft 70 is mounted onto the balloon by various methods known in the art. Optionally, a sheath can be extended over the stent (various designs and methods are known in the art).

To summarize use of the embodiments of the present invention described above, a guidewire is first laid in place within a corporeal lumen through any of the means well-known in the art. With use of an advancement member, a tracking member or folded balloon is advanced into the corporeal lumen over the guidewire. As the advancement member or folded balloon is advanced into the corporeal lumen, an inflatable balloon is pulled along with it by virtue of the attachment of its distal end to the tracking member or the advancement member. Once the inflatable balloon is in a desired position within the corporeal lumen, the balloon is inflated via the inflation means and hub.

It is contemplated that the tracking member can be varied to provide alternative embodiments of the catheter system of the invention. For example, the length of the tracking member may either be made longer or shorter. In the embodiment of the invention shown in FIG. 2, the tracking means has been shortened to a loop 18. Alternatively, it is contemplated that the tracking member may extend as an elongated tubular member the full length of system, from a proximal position outside the body lumen all the way to its distal end, to allow fluid administration of the treatment site. Also, the distal end of the advancement member could extend distally of the tracking member. Moreover, in one embodiment of the invention the inflatable balloon may be detachable.

In addition, it is contemplated that the tracking member may be single-lumen, so that it accommodates only a guidewire, or it may be multi-lumen, so that it can perform other functions as well. For example, the multi-lumen tracking member 19 shown in FIG. 4 contains lumen 3 for advancing over guidewire 9 and lumen 20, which provides a convenient means for attachment to advancement member 5. Advancement member 5 may be hollow to provide an alternative means for fluid administration to the treatment site. Lumen 20 may be open at the distal end 4 of tracking member 19, and tracking member 19 may alternatively have side holes 21 which provide communication from lumen 20 to the exterior of tracking member 19. Tracking member 19 may also be enlarged and/or lengthened to facilitate perfusion during balloon inflation.

Figure 6:
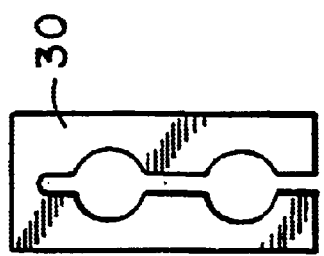
FIG. 6 is a cross-sectional view of a clamping member used in the FIG. 5 embodiment.

It is further contemplated that, in some applications, it may be deemed desirable to provide one or more additional attachment points between the inflation channel and the advancement member at various locations along the advancement member's length. A preferred method of attachment employs a removable clamping member 22 as shown in FIGS. 5 and 6. Clamping member 22 holds inflation channel 15 stationary with respect to advancement member 5 during withdrawal of catheter system 1. Clamping member 22 is preferably removed or loosened during catheter system advancement to optimize the pulling forces on the balloon. It is contemplated that in some instances more than one clamp 22 might be used.

Further, it is envisioned that the inflatable balloon and the inflation channel may be formed from the same material or they may be formed independently and subsequently attached by suitable known means. In addition, the distal extension of the balloon may be molded or otherwise formed to the shape of the tracking member.

In yet another alternative preferred embodiment of the invention, the advancement member and the tracking member may be formed in multiple segments each having varying mechanical properties which will allow for the customization of the catheter to a particular need.

The catheter systems of the present invention provides the user with a number of significant advantages not otherwise obtainable with currently available catheters. For example, they are less bulky than other available catheter systems and thus the balloon is able to move against resistance more easily, which allows less traumatic crossing of restrictions. Also, pushing on the advancement member has the effect of pulling the balloon along through the stenosis, and avoids the problem of bunching or gathering which occurs with other catheters. With a thin film balloon and inflation channel there is no dead space or volume that needs to be evacuated prior to use; therefore, little or no preparation is required. The smaller profile of the catheter system of the invention allows the inflatable balloon to be passed through stents easily. Partial inflation of the inflatable balloon can grab a previously inserted stent and facilitate retrieval of the stent. The smaller profile also permits passage through displaced stent struts.

Separating the inflatable balloon from a catheter shaft allows greater design flexibility to allow one to provide catheter systems with improved handling characteristics, and the fewer bonds between the balloon and the advancement shaft results in greater reliability. The simplicity of construction of the system of the present invention results in lower manufacturing costs. For example, fewer bonding operations are required, and expensive balloon folding processes can be avoided. Inflating the balloon against the advancement member or tracking member provides a focused force to enable the user to crack hard lesions at low pressure before the balloon is fully inflated. Doing so would allow vessel stretching to occur at a lower strain rate, which would minimize the trauma associated with balloon dilatation. With a guidewire in place, the balloon can be inflated additionally against the guidewire, thus providing an additional area of focused force.

A further advantage of the present invention is that the design allows additional catheters or devices to be placed over the guidewire adjacent to the inflatable balloon, and to be exchanged without first removing the catheter system. In addition, the advancement member may also act as an additional guidewire. For example, while balloon catheter 1 is in place within a vascular lesion, a second dilatation system or catheter may be advanced over the advancement member and its balloon positioned along side the first balloon (to increase the effective diameter of the dilatation) or adjacent to the first balloon (to increase the effective length of the dilatation). An imaging catheter such as an intravascular ultrasound catheter may be placed next to the first balloon to access the progress of the treatment without removing the balloon. A drug delivery catheter may be utilized in this manner, and the balloon of system 1 may be inflated at low pressure to provide vascular occlusion to improve the efficacy of the drug delivery. Likewise, various other catheters and devices may be suitably employed.

Figure 8:
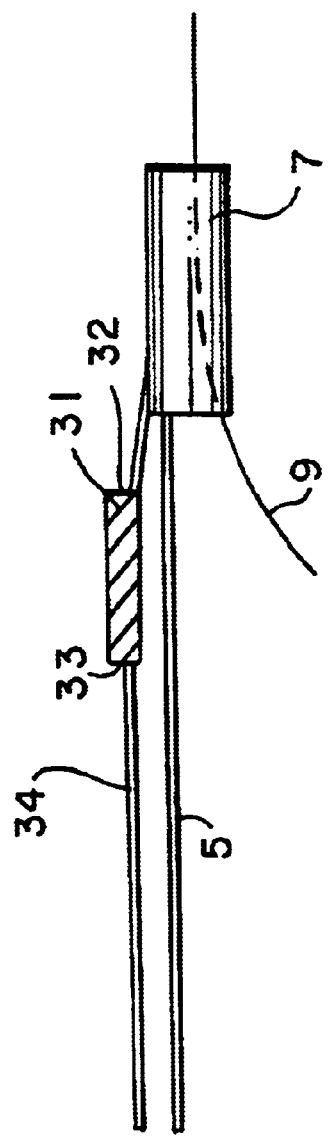
FIGS. 7 and 8 are each a schematic, lateral view of an additional embodiment of the invention.

Although the discussion above has been concerned with inflatable balloon systems and/or catheters, other types of catheters or systems may embody the present invention as schematically illustrated in FIG. 8. In FIG. 8, advancement member 5 terminates in a tubular tracking member 7, which tracks over guidewire 9. Distal end 32 of instrumentality 31 is attached to tracking member 7. Proximal end 33 of instrumentality 31 is unattached to either advancement member 5 or tracking member 7. Instrumentality 31 may be a laser, infusion tube, suction device, atherectomy means, other stent expansion means or another therapeutic or diagnostic apparatus. As required, a connecting member 34 may be attached to instrumentality 31. Connecting member 34 may be an electrical conducting wire, optical fiber, tube, or the like.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention, which, as a matter of language, might be said to fall therebetween.

What is claimed is:

1. A balloon dilatation catheter system comprising:
  a flexible elongated advancement member having a distal end,
  a tracking member having a proximal end and a distal end, said tracking member being adapted to slide over a guidewire and being fixedly attached to the distal end of the advancement member,
an inflation channel, and
an inflatable dilatation balloon having proximal end and distal end, the proximal end of the balloon being in fluid communication with the inflation channel,
wherein the distal end of the balloon is attached to the tracking member, an alignment member aligns the advancement member and the inflation channel in the longitudinal direction, and the advancement member is attached to or integral with the alignment member.

2. The catheter system of claim 1, wherein the tracking member comprises two or more lumens.

3. The catheter system of claim 1, wherein the dilatation balloon is attached to the distal end of the tracking member.

4. The catheter system of claim 1, wherein the dilatation balloon is attached to the proximal end of the tracking member.

5. The catheter system of claim 1, wherein the tracking member has a lubricious coating.

6. The catheter system of claim 1, wherein the tracking member is formed integral with the dilatation balloon.

7. A balloon dilatation catheter system comprising:
a flexible elongated advancement member having a distal end,
a dilatation balloon having a proximal end and a distal end, and
an inflation channel, the proximal end of the balloon being in fluid communication with the inflation channel,
wherein the distal end of the balloon is attached to the distal end of the advancement member, an alignment member aligns the advancement member and the inflation channel in the longitudinal direction, and the advancement member is attached to or integral with the alignment member.

8. The catheter system of claim 1 or 7, wherein the inflation channel is substantially coextensive with the advancement member.

9. The catheter system of claim 1 or 7, wherein the inflation channel is in a spiral configuration around the advancement member.

10. The catheter system of claim 1 or 7, wherein the advancement member comprises a flexible wire or hypotube.

11. The catheter system of claim 1 or 7, wherein the advancement member is rigid at its proximal end and increasingly more flexible as it extends distally.

12. The catheter system of claim 1 or 7, wherein the inflation channel is collapsible or noncollapsible.

13. The catheter system of claim 1 or 7, wherein the dilatation balloon or the inflation channel, or both, have a wire reinforcement.

14. The catheter system of claim 1 or 7, wherein the dilatation balloon and the inflation channel are formed integrally.

15. The catheter system of claim 1 or 7, wherein the inflation channel is attached to the advancement member at at least one point.

16. The catheter system of claim 1 or 7, which also comprises a torquer attached to the proximal end of the advancement member.

17. The catheter system of claim 1 or 7, wherein the inflation channel is not attached to the advancement member.

18. The catheter system of claim 1 or 7, wherein the balloon and/or the inflation channel are attached to the advancement member.

19. The catheter system of claim 1, wherein the advancement member is attached to the inner surface of the alignment member.

20. The catheter system of claim 1, wherein the advancement member is attached to the outer surface of the alignment member.

21. The catheter system of claim 1 or 7, wherein the alignment member is a hypotube.

22. A method of positioning the distal end of a dilatation system at a desired location within a patient's body, which comprises the steps of:
(a) advancing a first dilatation system comprising:
a flexible elongated advancement member having a distal end,
a tracking member having a proximal end and a distal end, said tracking member being adapted to slide over a guidewire and being fixedly attached to the distal end of the advancement member,
an inflation channel, and
an inflatable dilatation balloon having proximal end and distal end, the proximal end of the balloon being in fluid communication with the inflation channel,
wherein the distal end of the balloon is attached to the tracking member, and an alignment member aligns the advancement member and the inflation channel in the longitudinal direction,
over a guidewire through a corporeal lumen so that the distal end of said dilatation system is positioned at a desired location, and
(b) advancing another dilation system or other medical device over the guidewire to a position adjacent to said first dilation system.

23. A medical delivery system comprising:
a flexible elongated advancement member having a distal end,
a tracking member having a proximal end and a distal end, said tracking member being adapted to slide over a guidewire and being fixedly attached to the distal end of the advancement member, and
a medical instrumentality having proximal end and distal end, the proximal end of the instrumentality being in communication with a source,
wherein the distal end of the medical instrumentality is attached to the tracking member, an alignment member aligns the advancement member and any communication member connected to the medical instrumentality, and the advancement member is attached to or integral with the alignment member.

24. The delivery system of claim 23, wherein the tracking member comprises two or more lumens.

25. The delivery system of claim 23, wherein the medical instrumentality is attached to the distal end of the tracking member.

26. The delivery system of claim 23, wherein the medical instrumentality is attached to the proximal end of the tracking member.

27. The delivery system of claim 23, wherein the tracking member has a lubricious coating.

28. The delivery system of claim 23, wherein the tracking member is formed integral with the medical instrumentality.

29. A medical delivery system comprising:
a flexible elongated advancement member having a distal end,
a medical instrumentality having a proximal end and a distal end, and
a communication member, the proximal end of the medical instrumentality being in communication with the communication member, wherein the distal end of the medical instrumentality is attached to the distal end of the advancement member, an alignment member aligns the advancement member and the communication member in the longitudinal direction and the advancement member is attached to or integral with the alignment member.

30. The delivery system of claim 23 or 29, wherein the communication member is substantially coextensive with the advancement member.

31. The delivery system of claim 23 or 29, wherein the communication member is in a spiral configuration around the advancement member.

32. The delivery system of claim 23 or 29, wherein the advancement member comprises a flexible wire or hypotube.

33. The delivery system of claim 23 or 29, wherein the advancement member is rigid at its proximal end and increasingly more flexible as it extends distally.

34. The delivery system of claim 23 or 29, wherein the medical instrumentality and the communication member are formed integrally.

35. The delivery system of claim 23 or 29, wherein the communication member is attached to the advancement member at at least one point.

36. The delivery system of claim 23 or 29, wherein the communication member is not attached to the advancement member.

37. The delivery system of claim 23 or 29, wherein the medical instrumentality and/or the communication member are attached to the advancement member.

38. The catheter system of claim 1, wherein the advancement member is attached to the inner surface of the alignment member.

39. The catheter system of claim 1, wherein the advancement member is attached to the outer surface of the alignment member.

40. The delivery system of claim 23 or 29, wherein the alignment member is a hypotube.

41. A method of positioning the distal end of a medical instrumentality at a desired location within a patient's body, which comprises the steps of:
（a) advancing a delivery system comprising:
a flexible elongated advancement member having a distal end,
a tracking member having a proximal end and a distal end, said tracking member being adapted to slide over a guidewire and being fixedly attached to the distal end of the advancement member, and
a first medical instrumentality having proximal end and distal end, the proximal end of the instrumentality being in communication with a source,
wherein the distal end of the medical instrumentality is attached to the tracking member and an alignment member aligns the advancement member and any communication member connected to the first medical instrumentality,
over a guidewire through a corporeal lumen so that the first medical instrumentality is positioned at a desired location, and
(b) advancing a second medical instrumentality distally over the guidewire to a position adjacent to the delivery system.

42. A method of positioning the distal end of a dilatation system at a desired location within a patient's body, which comprises the steps of:
(a) advancing a dilatation system comprising:
a flexible elongated advancement member having a distal end,
a dilatation balloon having a proximal end and a distal end, and
an inflation channel, the proximal end of the balloon being in fluid communication with the inflation channel,
wherein the distal end of the balloon is attached to the distal end of the advancement member and an alignment member aligns the advancement member and the inflation channel in the longitudinal direction,
over a guidewire through a corporeal lumen so that the distal end of said dilatation system is positioned at a desired location, and
(b) advancing another dilatation system or other medical device over the guidewire to a position adjacent to the catheter system.

43. A method of positioning the distal end of a medical instrumentality at a desired location within a patient's body, which comprises the steps of:
(a) advancing a delivery system comprising:
a flexible elongated advancement member having a distal end,
a first medical instrumentality having a proximal end and a distal end, and
a communication member, the proximal end of the medical instrumentality being in communication with the communication member,
wherein the distal end of the first medical instrumentality is attached to the distal end of the advancement member and an alignment member aligns the advancement member and the communication member in the longitudinal direction,
over a guidewire through a corporeal lumen so that the distal end of said dilatation system is positioned at a desired location, and
(b) advancing a second medical instrumentality over the guidewire to a position adjacent to the delivery system.

* * * * *